United States Patent
Mo et al.

(10) Patent No.: US 7,627,386 B2
(45) Date of Patent: Dec. 1, 2009

(54) ULTRASOUND IMAGING SYSTEM PARAMETER OPTIMIZATION VIA FUZZY LOGIC

(75) Inventors: Larry Y. L. Mo, San Ramon, CA (US);
Glen W. McLaughlin, Saratoga, CA (US); Brian Derek DeBusschere, Orinda, CA (US); Ting-Lan Ji, San Jose, CA (US); Ching-Hua Chou, Mountain View, CA (US); David J. Napolitano, Pleasanton, CA (US); Kathy S. Jedrzejewicz, Austin, TX (US); Thomas Jedrzejewicz, Austin, TX (US); Kurt Sandstrom, San Jose, CA (US); Feng Yin, Palo Alto, CA (US); Scott Franklin Smith, Oak Creek, WI (US); Wenkang Qi, Cupertino, CA (US); Robert Stanson, LaSalle (CA)

(73) Assignee: Zonaire Medical Systems, Inc., Mountain View, CA (US)

( * ) Notice: Subject to any disclaimer, the term of this patent is extended or adjusted under 35 U.S.C. 154(b) by 707 days.

(21) Appl. No.: 10/961,709

(22) Filed: Oct. 7, 2004

(65) Prior Publication Data
US 2006/0079778 A1    Apr. 13, 2006

(51) Int. Cl.
*G05B 13/02* (2006.01)
(52) U.S. Cl. .................. 700/50; 600/437; 600/443; 600/457; 600/441
(58) Field of Classification Search .............. 702/39; 600/441, 450, 455, 456, 407, 453, 454, 437, 600/443; 700/50; 73/625, 626; 382/128
See application file for complete search history.

(56) References Cited

U.S. PATENT DOCUMENTS

| | | | |
|---|---|---|---|
| 4,852,576 A | 8/1989 | Inbar et al. | |
| 5,260,871 A | 11/1993 | Goldberg | |
| 5,269,289 A * | 12/1993 | Takehana et al. | 600/109 |
| 5,313,948 A | 5/1994 | Murashita et al. | |
| 5,357,965 A | 10/1994 | Hall et al. | |
| 5,566,674 A | 10/1996 | Weng | |
| 5,579,768 A | 12/1996 | Klesenski | |
| 5,654,509 A | 8/1997 | Miele et al. | |
| 5,776,063 A | 7/1998 | Dittrich et al. | |
| 5,782,766 A | 7/1998 | Weng et al. | |

(Continued)

*Primary Examiner*—Brian Casler
*Assistant Examiner*—Joel M Lamprecht
(74) *Attorney, Agent, or Firm*—Townsend and Townsend and Crew LLP (57) ABSTRACT

An ultrasound scanner is equipped with one or more fuzzy control units that can perform adaptive system parameter optimization anywhere in the system. In one embodiment, an ultrasound system comprises a plurality of ultrasound image generating subsystems configured to generate an ultrasound image, the plurality of ultrasound image generating subsystems including a transmitter subsystem, a receiver subsystem, and an image processing subsystem; and a fuzzy logic controller communicatively coupled with at least one of the plurality of ultrasound imaging generating subsystems. The fuzzy logic controller is configured to receive, from at least one of the plurality of ultrasound imaging generating subsystems, input data including at least one of pixel image data and data for generating pixel image data; to process the input data using a set of inference rules to produce fuzzy output; and to convert the fuzzy output into numerical values or system states for controlling at least one of the transmit subsystem and the receiver subsystem that generate the pixel image data.

23 Claims, 4 Drawing Sheets

U.S. PATENT DOCUMENTS

| | | | |
|---|---|---|---|
| 5,799,111 A * | 8/1998 | Guissin | 382/254 |
| 5,857,973 A | 1/1999 | Ma et al. | |
| 5,871,019 A | 2/1999 | Belohlavek | |
| 5,935,074 A | 8/1999 | Mo et al. | |
| 5,954,653 A | 9/1999 | Hatfield et al. | |
| 5,984,870 A | 11/1999 | Giger et al. | |
| 6,036,643 A | 3/2000 | Criton et al. | |
| 6,068,598 A | 5/2000 | Pan et al. | |
| 6,102,859 A | 8/2000 | Mo | |
| 6,110,119 A | 8/2000 | Hall | |
| 6,113,544 A | 9/2000 | Mo | |
| 6,120,446 A | 9/2000 | Ji et al. | |
| 6,142,943 A | 11/2000 | Mo et al. | |
| 6,162,176 A | 12/2000 | Washburn et al. | |
| 6,312,385 B1 | 11/2001 | Mo et al. | |
| 6,315,728 B1 | 11/2001 | Muzilla et al. | |
| 6,322,509 B1 | 11/2001 | Pan et al. | |
| 6,358,205 B1 | 3/2002 | Ustuner et al. | |
| 6,390,983 B1 | 5/2002 | Mo et al. | |
| 6,398,733 B1 | 6/2002 | Simopoulos et al. | |
| 6,423,003 B1 | 7/2002 | Ustuner et al. | |
| 6,434,262 B2 | 8/2002 | Wang | |
| 6,464,637 B1 | 10/2002 | Criton et al. | |
| 6,464,640 B1 | 10/2002 | Guracar et al. | |
| 6,464,641 B1 | 10/2002 | Pan et al. | |
| 6,468,218 B1 | 10/2002 | Chen et al. | |
| 6,491,636 B2 | 12/2002 | Chenal et al. | |
| 6,497,661 B1 | 12/2002 | Brock-Fisher | |
| 6,503,203 B1 | 1/2003 | Rafter et al. | |
| 6,512,854 B1 | 1/2003 | Mucci et al. | |
| 6,547,737 B2 * | 4/2003 | Njemanze | 600/454 |
| 6,577,967 B2 | 6/2003 | Mo et al. | |
| 6,932,770 B2 * | 8/2005 | Hastings et al. | 600/443 |

* cited by examiner

ULTRASOUND IMAGING SYSTEM PARAMETER OPTIMIZATION VIA FUZZY LOGIC

CROSS-REFERENCES TO RELATED APPLICATIONS

Not Applicable

BACKGROUND OF THE INVENTION

This invention relates generally to ultrasound imaging systems and, more particularly, to adaptive optimization of ultrasound imaging system parameters using fuzzy logic controllers or neural network or both.

Diagnostic Ultrasound Imaging

Medical ultrasound imaging systems need to support a set of imaging modes for clinical diagnosis. The basic imaging modes are timeline Doppler, color flow velocity and power mode, B mode, and M mode. In B mode, the ultrasound imaging system creates two-dimensional images of tissue in which the brightness of a pixel is based on the intensity of the return echo. In color flow imaging mode, the movement of fluid (e.g., blood) or tissue can be imaged. Measurement of blood flow in the heart and vessels using the Doppler effect is well known. The phase shift of backscattered ultrasound waves can be used to measure the velocity of the moving tissue or blood. The Doppler shift may be displayed using different colors to represent speed and direction of flow. In the spectral Doppler imaging mode, the power spectrum of these Doppler frequency shifts is computed for visual display as velocity-time waveforms.

State-of-the-art ultrasound scanners may also support advanced or emerging imaging modes including contrast agent imaging, 3D imaging, spatial compounding, and extended field of view. Some of these advanced imaging modes involve additional processing of images acquired in one or more basic imaging modes, and attempt to provide enhanced visualization of the anatomy of interest.

A new trend in ultrasound technology development is the emergence of compact or portable ultrasound scanners that leverage the unceasing advances in system-on-a-chip technologies. It is anticipated that these compact scanners, though battery-operated, will support more and more of the imaging modes and functions of conventional cart-based scanners.

Regardless of physical size, ultrasound imaging systems are comprised of many subsystems. As shown in the ultrasound imaging system 10 of FIG. 1, the main signal path includes the transducer 12 with switch 13, transmitter 14, receiver 16, image processor(s) 18, display system 20, master controller 22, and user-input system 24. The transmitter 14, probe 12, and receiver subsystems 16 are responsible primarily for the acquisition, digitization, focusing and filtering of echo data. The image processing block 18 performs detection (e.g., echo amplitude for B-mode, mean velocity for color flow mode), and all subsequent pixel data manipulation (filtering, data compression, scan conversion and image enhancements) required for display. As used herein, the term pixel (derived from "picture element") image data simply refers to detected image data, regardless of whether it has been scan converted into an x-y raster display format.

Conventional ultrasound systems generally require optimal adjustments of numerous system parameters involved in a wide range of system operations from data acquisition, image processing, and audio/video display. These system parameters can be divided into two broad categories: 1) user-selectable or adjustable; and 2) engineering presets. The former refers to all system parameters that the user can adjust via the user control subsystem. This includes imaging default parameters (e.g., gray map selection) that the user can program via the user control subsystem and store in system memory. In contrast, "engineering presets" refer a wide range of system processing and control parameters that may be used in any or all of the major subsystems for various system operations, and are generally pre-determined and stored in system memory by the manufacturer. These may include control or threshold parameters for specific system control mechanisms and/or data processing algorithms within various subsystems.

The need to optimize both kinds of system parameters is a long-standing challenge in diagnostic ultrasound imaging, mainly because (1) the majority of sonographers or users often lack the time and/or training to properly operate a very broad range of user-controls for optimal system performance; and (2) engineering presets are usually pre-determined by the manufacturer based on "typical" or "average" system operating conditions including patient type (body size and fat/muscle composition), normal and abnormal tissue characteristics for various application types, and environmental factors (e.g., ambient light condition).

For a compact scanner, user-control design is particularly challenging because the space available on the console for imaging control keys can be very limited. This means that the overall user-control subsystem will be restricted and/or more difficult to use (e.g., accessing multiple layers of soft-key menus) compared to conventional cart-based scanners.

Another related challenge for all ultrasound scanners is ergonomics. Even for an expert sonographer who is proficient at using all of the available system controls, the repetitive hand motions required to scan with a probe, and to adjust many control keys for each ultrasound examination protocol, are widely recognized as a source of repetitive stress injuries for sonographers.

There is need for more automated control of imaging parameters in ultrasound systems.

Fuzzy Logic Control

As taught by B. Kosko (Neural Networks and Fuzzy Systems, Prentice Hall, 1992), fuzzy logic is a methodology for estimating input-output functions that has proven very effective for "intelligent" control of a wide range of non-linear systems from subway system traffic to auto-focusing in camcorders. Fuzzy logic is especially suited to controlling systems whose inputs are multi-valued, or belong simultaneously to two or more contradictory sets of values (hence the name "fuzzy"). In fact, inputs in a fuzzy system are classified as members of different fuzzy sets with various degrees of membership. A key property of fuzzy inputs is that they exhibit continuous gradations between overlapping classes. As an example, precipitation can be classified as dense fog, drizzle, light rain, heavy rain, and downpour. Note that fuzzy terms are italicized throughout this disclosure.

Unlike statistical estimators, the fuzzy approach estimates a function without a mathematical model of how outputs depend on inputs. Instead, the mapping from inputs to outputs is defined by a set of linguistic rules or memory associations, similar to what an expert user would do. A fuzzy traffic controller might contain the fuzzy association "If traffic is heavy in this direction, then keep the light green longer." One method of establishing the fuzzy rules is to pool the knowledge of many experts, and directly program them into the fuzzy controller. This is known as the Fuzzy Expert System approach.

For some applications, however, it is very difficult even for experts to articulate a set of rules that define the desired input-output behavior. For example, who can define a tree, a bomb, or his or her own face to the satisfaction of an automated detection system? Instead of using the fuzzy approach, such ill-defined problems may be better handled by a related but different methodology known as neural network. As taught by Kosko, neural network is a signal processing method that differs from fuzzy expert system in the way it associatively "inferences" or maps inputs to outputs. The neural approach requires the specification of a nonlinear dynamical system, the acquisition of a sufficiently representative set of numerical training samples, and the encoding of those training samples in the dynamical system by repeated learning cycles. In simple terms, the neural approach mimics how the neurons in the human brain conduct a learning process: it avoids direct definition but learns by pointing out examples.

Adaptive Ultrasound Imaging

Figure 1:
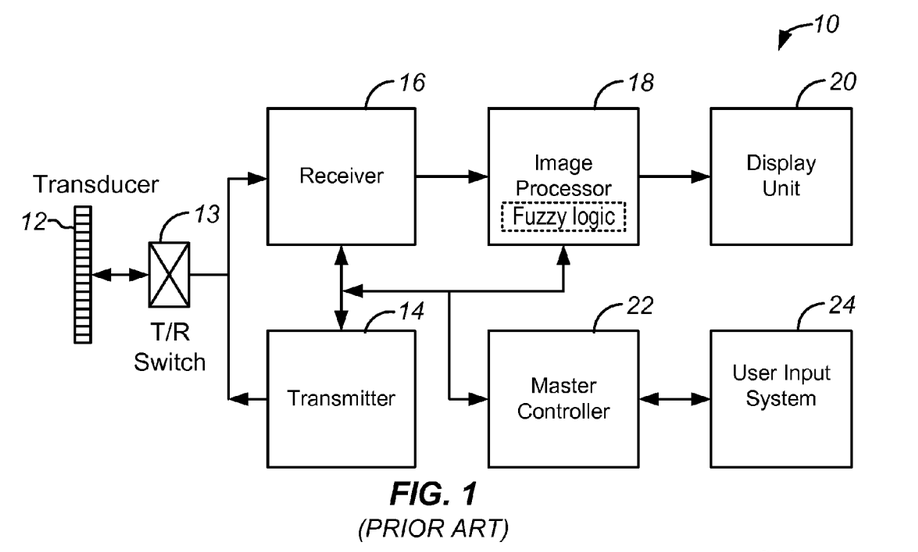
FIG. 1 is a block diagram of a conventional ultrasound scanner.

Automatic system optimization techniques that can adapt to received ultrasound data and/or prevailing system operating conditions have received increasing attention in recent years. Referring to FIG. 1, these typically entail analyzing the pixel image data from the image processing unit 18, and adjusting different system parameters via, for example, the master controller 22. U.S. Pat. No. 6,398,733, for example, assumes that there exists a single optimal or correct answer and attempt to achieve that pre-determined optimal state based on mathematical or statistical methods, and binary logical decisions (e.g., "noise" or "tissue") that utilize a set of fixed threshold values.

In reality, however, many of the inputs required for system or imaging control in an ultrasound system are not "black or white," but are fuzzy: showing "many shades of gray" within overlapping classes. For example, the echo quality in a particular region of a gray-scale B-image can be classified as noisy echo, or strong echo. There is a need to develop more robust automatic system control methods that will work well with fuzzy input and/or output variables.

Although fuzzy logic and neural networks have been proposed for use in diagnostic ultrasound imaging systems, the existing technique is limited to computerized classification or segmentation of pixel image data within the image processing block 18 (see rectangle in dashed line of FIG. 1). Since the treatment of different pixels are often directly dependent on how they are classified, fuzzy logic provides a way of making decisions that can minimize false classifications. Examples include B-mode versus color flow data segmentation, and image registration for spatial compounding or 3D reconstruction.

BRIEF SUMMARY OF THE INVENTION

Embodiments of the present invention provide an ultrasound scanner equipped with one or more fuzzy control units that can perform adaptive system parameter optimization anywhere in the system from top-level control operations to the lowest hardware and/or software algorithm control operations. As used herein, the term "fuzzy controller" refers to an adaptive signal processor that employs primarily the fuzzy expert system approach. Optionally, the system may also invoke a separate neural network processor to perform certain functions separately or in conjunction with the fuzzy controller.

In accordance with an aspect of the present invention, an ultrasound system comprises a plurality of ultrasound image generating subsystems configured to generate an ultrasound image, the plurality of ultrasound image generating subsystems including a transmitter subsystem, a receiver subsystem, and an image processing subsystem; and a fuzzy logic controller communicatively coupled with at least one of the plurality of ultrasound imaging generating subsystems. The fuzzy logic controller is configured to receive, from at least one of the plurality of ultrasound imaging generating subsystems, input data including at least one of pixel image data and data for generating pixel image data; to process the input data using a set of inference rules to produce fuzzy output; and to convert the fuzzy output into numerical values or system states for controlling at least one of the transmit subsystem and the receiver subsystem that generate the pixel image data.

In some embodiments, the set of inference rules used by the fuzzy logic controller are derived from at least one of (i) a predefined expert system that represents what an expert sonographer or a system engineer would do to control operations of at least one of the plurality of ultrasound image generating subsystems; and (ii) a neural network which can be trained to adapt functions of at least one of the ultrasound image generating subsystems. A neural network processor is communicatively coupled with the fuzzy logical controller and at least one of the ultrasound image generating subsystems. The neural network processor is configured to adapt functions of at least one of the ultrasound image generating subsystems based on, for instance, at least one of different patient types, user preferences, and system operating conditions. The fuzzy logic controller is configured to fuzzify the input data prior to processing input data using the set of inference rules. Fuzzifying the input data comprises determining a degree of membership or membership value of the input data to a set of predefined input membership functions or classes.

In specific embodiments, the fuzzy logic controller is configured to adaptively adjust system parameters for at least one imaging mode. The fuzzy logic controller may be configured to adaptively adjust system parameters for a plurality of imaging modes, including transmit control, receiver gain control, receive focusing, and image processing parameters. For example, the system parameters include receiver gain control parameters for the receiver subsystem. The fuzzy logic controller is configured to adaptively adjust the receiver gain control parameters for the receiver subsystem to adjust the gain for different regions within the B-mode imaging. Adaptively adjusting the receiver gain control parameters for the receiver subsystem comprises: analyzing a pixel intensity distribution in different pre-defined regions (ROI) of a detected image received by the receiver subsystem, based on a most recently processed series of one or more image frames that have been processed by the image processing subsystem; for each ROI, computing a mean pixel intensity level and classifying the mean pixel intensity level based on a set of two or more predefined fuzzy membership functions for mean pixel intensity level; for each ROI, computing a percentage of pixels that have exceeded a system noise threshold and classifying the result based on a set of two or more predefined fuzzy membership functions for ROI composition; applying a set of inference rules to evaluate gain change membership values of a set of predefined gain change membership functions; defuzzifying the gain change membership values, by converting the gain change membership values into a numeric gain adjustment via a set of predefined equations that utilize the gain change membership values as weight factors, to obtain prescribed gain changes; and applying the prescribed gain changes to corresponding data segments for at least one or a current B-mode image frame and a future B-mode image frame. For example, the predefined fuzzy membership functions for mean pixel intensity level include "too dark," "just right," and "too bright"; the predefined fuzzy membership functions for ROI composition include "noise-dominant" and "echo-dominant"; and the predefined gain change membership functions include "positive," "zero," and "negative." In general, the gain changes may be effected at any point (analog or digital) in the data processing path.

In some embodiments, the image processing subsystem comprises a B-mode image processor including a detector, a log compression and filtering block, and a scan converter. The fuzzy logic controller is configured to read out the pixel image data from the B-mode image processor before (or after) the scan converter. The system parameters may further comprise at least one of: transmit control parameters for the transmitter subsystem to specify at least one of transmit waveform, aperture function, delay profile, and pulsed repetition frequency for one or more imaging modes; electronic array focusing parameters for the receiver subsystem to specify the receive aperture function as a function of time/depth and the time delay profiles for image reconstruction; and image processing parameters for the image processing subsystem to specify at least one of display dynamic range, gray or color maps, and spatial/temporal filtering. The plurality of ultrasound image generating subsystems further include a transducer subsystem and an audio and video display subsystem.

In accordance with another aspect of the invention, an ultrasound system comprises a plurality of ultrasound image generating subsystems configured to generate an ultrasound image, the plurality of ultrasound image generating subsystems including a transmitter subsystem, a receiver subsystem, and an image processing subsystem; and a fuzzy logic controller communicatively coupled with at least one of the plurality of ultrasound imaging generating subsystems. The fuzzy logic controller includes a fuzzy logic program stored in a computer readable storage medium. The fuzzy logic program includes code for receiving, from at least one of the plurality of ultrasound imaging generating subsystems, input data including at least one of pixel image data and data for generating pixel image data; code for processing the input data using a set of inference rules to produce fuzzy output; and code for converting the fuzzy output into numerical values or system states for controlling at least one of the transmit subsystem and the receiver subsystem that generate the pixel image data.

In some embodiments, a neural network processor is communicatively coupled with the fuzzy logical controller and at least one of the ultrasound image generating subsystems. The neural network processor includes a neural network program stored in a computer-readable storage medium. The neural network program has code for adapting functions of at least one of the ultrasound image generating subsystems. The fuzzy logic program includes code for fuzzifying the input data prior to processing input data using the set of inference rules, and wherein fuzzifying the input data comprises determining a degree of membership or membership value of the input data to a set of predefined input membership functions or classes.

Another aspect of the invention is directed to a method of processing data for generating an ultrasound image. The method comprises receiving, from at least one of a plurality of ultrasound imaging generating subsystems which include a transmitter subsystem, a receiver subsystem, and an image processing subsystem, input data including at least one of pixel image data and data for generating pixel image data; processing the input data using a set of inference rules to produce fuzzy output; and converting the fuzzy output into numerical values or system states for controlling at least one of the transmit subsystem and the receiver subsystem that generate the pixel image data.

DETAILED DESCRIPTION OF THE INVENTION

Figure 2:
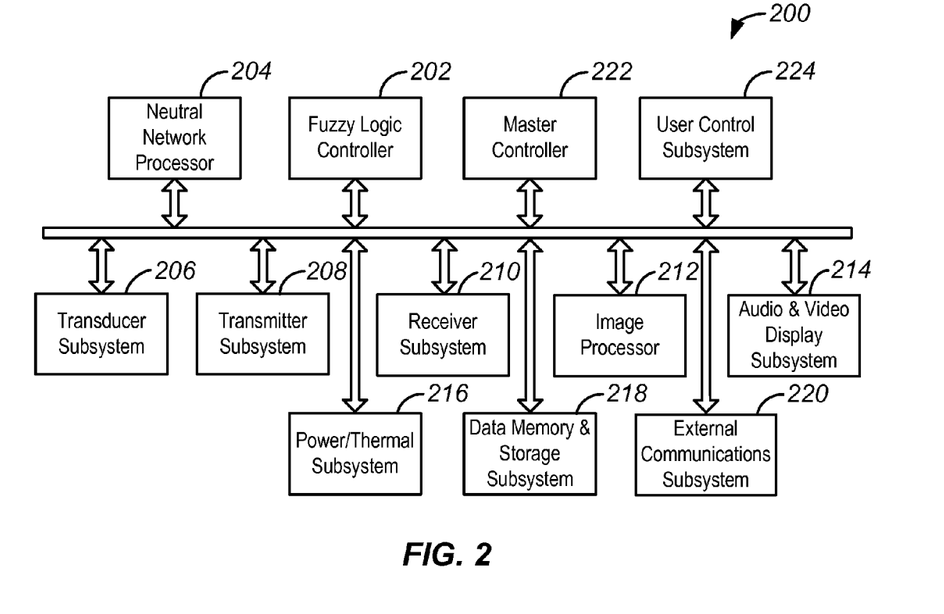
FIG. 2 is a block diagram of an ultrasound scanner equipped with a fuzzy logic controller and a neural network processor for automatic imaging parameter optimization according to an embodiment of the present invention.

Embodiment of the present invention provide an ultrasound scanner equipped with one or more fuzzy control units that can perform adaptive system parameter optimization anywhere in the system from top-level control operations to the lowest hardware and/or software algorithm control operations. FIG. 2 shows a block diagram of an ultrasound system 200 having a fuzzy logic controller 202. As used herein, the term "fuzzy controller" or "fuzzy logic controller" refers to an adaptive signal processor that employs primarily the fuzzy expert system approach. Optionally, the system may also invoke a separate neural network processor 204 to perform certain functions separately or in conjunction with the fuzzy controller 202. The inventors have found that many of the ultrasound imaging parameters outside of the image processing block 18 of FIG. 1, including both user-adjustable and engineering-presets, are best optimized using fuzzy logic, with or without the aid of a neural network. Neural networks are advantageously used for more challenging image analysis problems such as detection of anatomical features or abnormalities, and disease classification.

It is important not to confuse statistical analysis with fuzzy reasoning. Whereas statistical analysis has been widely used in ultrasound data processing, and is concerned with uncertainties in well-defined events or concepts, fuzzy reasoning is concerned with reasoning of fuzzy events or concepts.

For ultrasound imaging systems, potential applications of fuzzy control are innumerable because many system parameters from top system-level to algorithm-level are fuzzy by nature. That is, the inputs to the control unit are best classified in fuzzy terms, and the correct answer or acceptable output value is not a single state or numerical value, but rather a range of optimal values.

In the present embodiment of the ultrasound system 200 as seen in FIG. 2, the fuzzy control controller 202 is configured to interact with any to all of the major subsystems that are involved in image formation and storage. The major subsystems can be described as follows. The transducer subsystem 206 includes cables, probes, multiplexers, thermal sensors, and the like. The transmitter subsystem 208 contains pulsers including aperture and voltage controllers, and the like. The receiver subsystem 210 includes amplifiers, filters, demodulators, analog-to-digital conversion unit, image reconstruction (array focusing) module, and the like. The image processor 212 includes detectors for different modes, filters, scan converter, and the like. The audio and video display subsystem 214 includes amplifiers, filters and audio speakers, video processor, CRT and/or LCD display units, and the like. The power/thermal subsystem 216 provides power supplies to various subsystems, temperature sensors, cooling system, and the like. The data memory and storage subsystem 218 includes cine, memory devices/buffers, hard disks, micro-disks, and the like. The external communications subsystem 220 provide interfaces to (1) external storage or display devices including, for example, printer, VCR, DVD, MOD, workstation; (2) the Internet; (3) physiological trigger signals such as ECG; and the like. The master controller 222 is a dedicated processing unit such as a power PC, which coordinates and controls the activities of all subsystems. The master controller 222 can usually communicate either directly or indirectly with all subsystems in order to synchronize their activities (often with highly precise timing) for smooth system operations in various scanning modes. The user control subsystem 224 provides user control mechanisms and units including, for example, console, keyboard, hard and soft keys, touch screen, foot pedals, and voice control.

FIG. 2 shows only a general conceptual design in which all subsystems can communicate with and/or affect one another via system data bus(es), and timing and control signals and/or electrical power lines, as indicated by the two-way arrows. This is done for convenience and simplicity. In practice, the ultrasound data, control signal and electrical power distribution paths are part of the system architectural design, and the connectivity between different subsystems may be more restricted than that suggested by FIG. 2.

For many system optimization applications, the fuzzy controller 202 may receive inputs simultaneously from two or more subsystems, process the information, and subsequently affect the controls of one or more subsystems. Thus, compared to the previous approach that utilizes fuzzy logic only for pixel image analysis, this embodiment of the invention adds whole new dimensions of system control that is expected to significantly improve parameter optimization in any subsystem.

Figure 3:
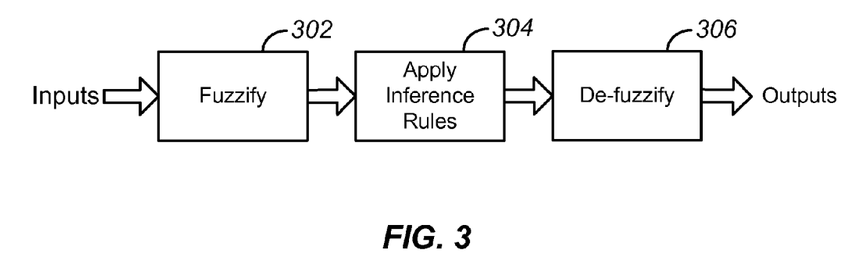
FIG. 3 is a schematic diagram illustrating the three main steps in fuzzy logic control according to an embodiment of the present invention.

In general, fuzzy logic control includes three main steps. As shown in FIG. 3, the first step is to fuzzify the inputs (step 302) which, depending on the application, may represent some numerical value derived from ultrasound image data, or data that represents the prevailing operating conditions of the system. As will be described in more detail later, fuzzifying an input numerical value (e.g., mean pixel value) involves determining its degree of membership, or membership value, to a set of predefined input membership functions or classes for pixel intensity (e.g., too dark, just right, too bright). The second step 304 is to apply a set of inference or IF-THEN rules, to evaluate membership values for all possible output membership functions. The third step 306 is to defuzzify the output membership values and derive from them a concrete numeric value (e.g., a gain change in dB) that will improve the quality of the image.

Ideally speaking, the inference rules represent the combined knowledge and reasoning or decision-making power of an expert sonographer and an ultrasound system engineer. The reference database of inference rules can be established by at least two methods:

1. Direct translation (database programming) of an expert's knowledge into a set of inference rules.
2. Use of neural networks that can be trained to learn, or capture the expert knowledge of how the user manually adjusts system parameters for different data sets. As shown in FIG. 2, this involves having a neural network processor 204 that can receive inputs from any to all of the subsystems during its "training period."

The fuzzy logic controller 202 and neural network processor 204 are desirably implemented in software using a database structure and a fast processor such as a power PC or a DSP chip(s). The processor may be dedicated to fuzzy logic control only, or it may be shared by other subsystems within the ultrasound system 200. One advantage of a software implementation is that the expert knowledge database can be more easily upgraded as the expert knowledge base, computing power and/or digital storage capacities (per unit cost) grow over time.

Depending on the specific application, the fuzzy controller 202 can be activated by a one-button-push per optimization cycle, or a one-button-push for continuous optimization (similar to the "cruise control" function of an automobile), and some of the optimization options may be software configurable.

The neural network processor 204, if available, can be activated anytime via the user-control subsystem 224 during a training period, or can be linked directly to the activation of certain system modes so as to undergo continuous learning.

Figure 4:
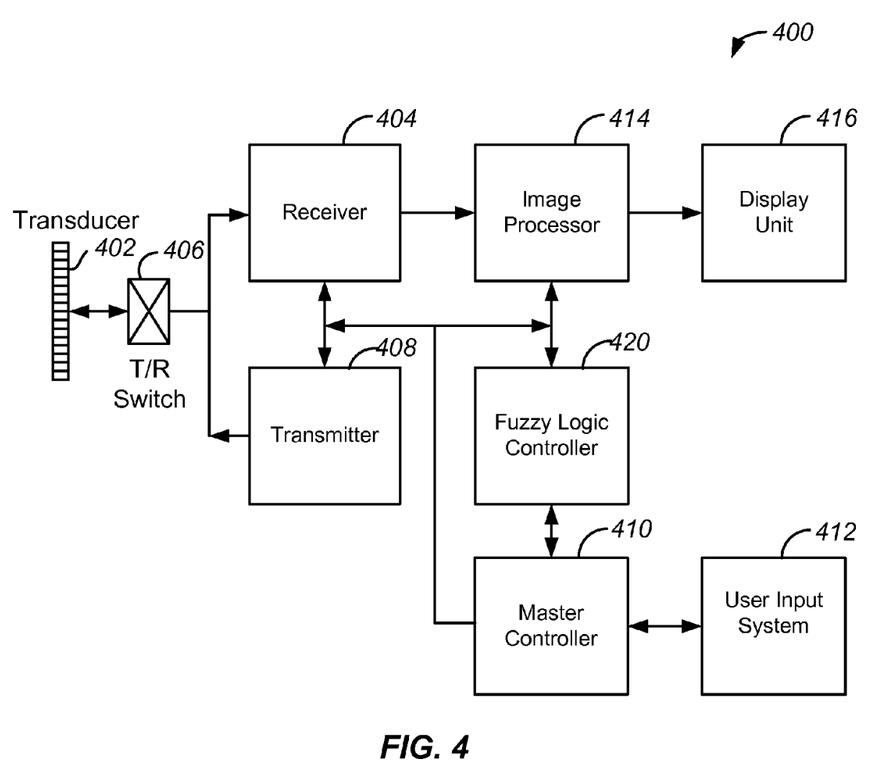
FIG. 4 is a block diagram of an ultrasound scanner equipped with a fuzzy logic controller according to another embodiment of the present invention.

FIG. 4 shows a specific embodiment of an ultrasound scanner 400 that incorporates various features of the present invention. The scanner 400 includes a transducer array 402 comprised of a plurality of separately driven transducer elements, each of which produces a burst of ultrasonic energy when energized by a pulsed waveform produced by a transmitter. The ultrasonic energy reflected back to the transducer array 402 from the object under study is converted to an electrical signal by each receiving transducer element and applied separately to a receiver 404 through a set of transmit/receive (T/R) switches 406. The transmitter 408, receiver 404, and switches 406 are operated under control of a master controller 410 responsive to commands from user inputs entered through the user input system 412. An image processor 414 processes signals from the receiver 404 and sends the output to a display unit 416 such as an LCD or CRT monitor. A fuzzy logic controller 420 communicates with the various components of the scanner 400 via bus(es), signal/data line(s), and the like.

A complete scan is performed by acquiring a series of echoes in which switches are set to their transmit position, the transmitter 408 is gated ON momentarily to energize each transducer element of the transducer 402, the switches 406 are then set to their receive position, and the subsequent echo signals detected by each transducer element are applied to receiver 404, which amplifies, filters, digitizes and combines the separate echo signals from each transducer element to produce a set of echo-location image data.

Within the receiver 404, the echo-location image data may be down-shifted in frequency to produce their in-phase/quadrature (I/Q) components. Depending on the scan mode, the I/Q data is converted into respective B, color flow, B flow or spectral Doppler images in the image processor 414, which outputs raster-scan images to the display unit 416.

Embodiments of the present invention can be divided into a number of functional categories including adaptive image optimization for B, color flow and spectral Doppler modes, and adaptive control of various subsystems. In the ultrasound scanner of FIG. 4, the fuzzy controller 420 is configured to perform mainly image optimization functions. Specifically, based on pixel image data from the image processor 414, the fuzzy controller 420 can automatically adjust parameters in the transmitter 408, receiver 404, and/or image processor 414 directly through signal/data paths or indirectly through the master controller 410. By automating the user-controls based on actual image data, the efficiency, reproducibility, and ease of use of ultrasound scanner 400 can be significantly enhanced.

Examples of different functional aspects of the present invention are provided. They are meant to be representative, but not exhaustive, of the capabilities of adaptive parameter optimization using fuzzy logic control.

Adaptive Receiver Gain

Figure 5:
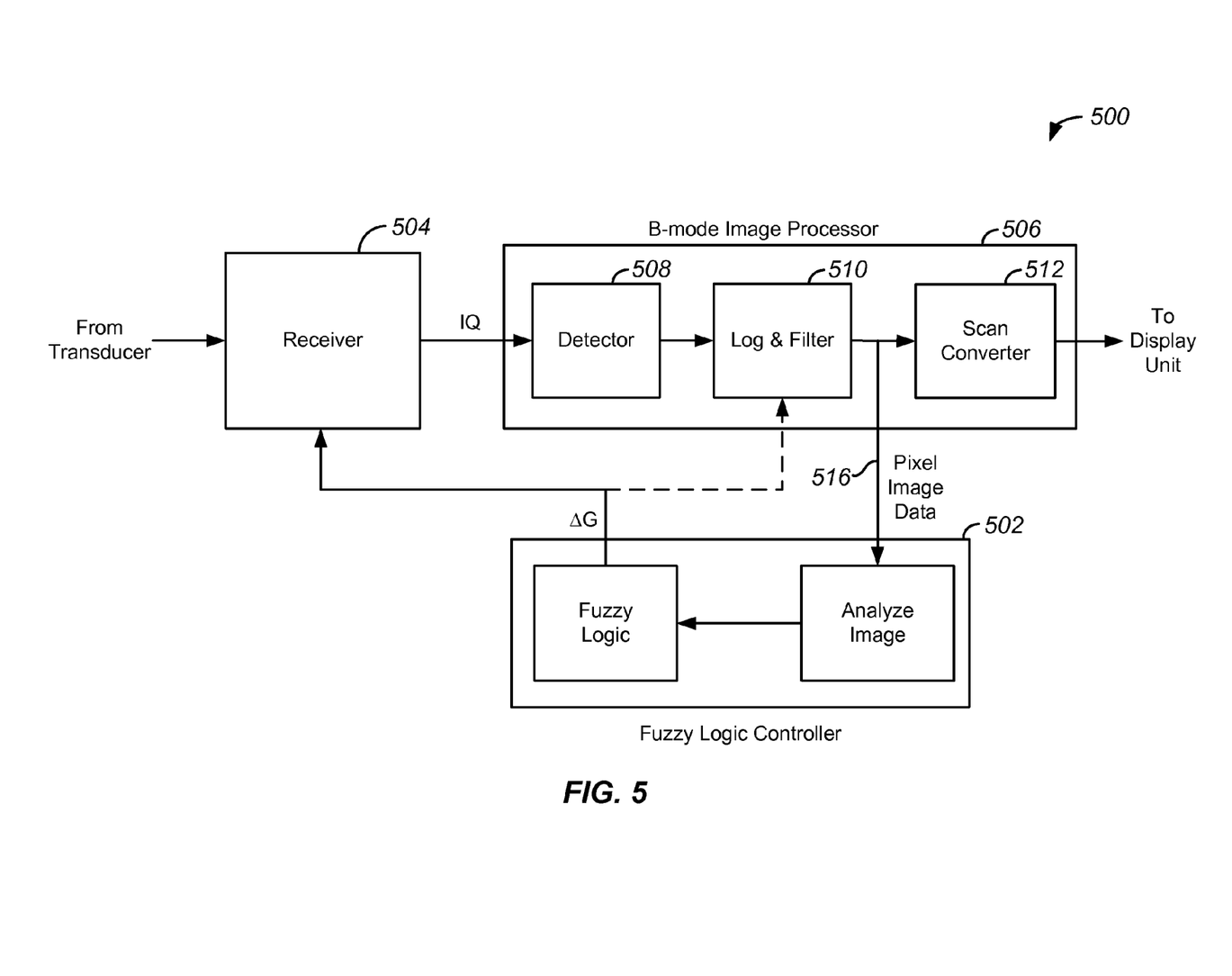
FIG. 5 is a block diagram of a receiver, the main processing blocks within a B-mode image processor, and a fuzzy logic controller according to a specific embodiment of the present invention.

To illustrate the main steps (FIG. 3) of fuzzy logic control, a specific example pertaining to adaptive receiver gain control in B-mode is first presented. FIG. 5 shows an imaging system 500 in which the fuzzy logic controller 502 is configured to control a signal amplifier within the receiver 504. The variable gain amplifier (not shown) may be analog or digital depending on its location within the signal processing chain. The B-mode image processor 506 comprises a detector 508, log compression & filtering block 510, and scan converter 512. The log compression block 510 compresses the dynamic range of the detected output ($I^2+Q^2$) for typically an 8-bit gray scale display that ranges from 0 to 255. The filter in the block 510 refers to 2D spatial filter and temporal filter to smooth out the image within each frame, and from frame to frame, respectively. Finally, the scan converter 512 transforms acoustic scan coordinates (scan angle and depth) into rectilinear coordinates for a raster-scan display.

It is noted that the fuzzy logic controller 502 reads out the pixel image data prior to scan conversion (see arrow 516). As a simple example, suppose the image data is characterized by its mean pixel value over a pre-determined region of interest (ROI), which may be a predefined 2D region (such as that controlled by a depth-gain-control slider on the front-panel) or the entire image frame. Clearly, if the mean pixel value is too large, the ROI is probably too bright, such that the gain needs to be reduced by an appropriate amount.

Figure 6:
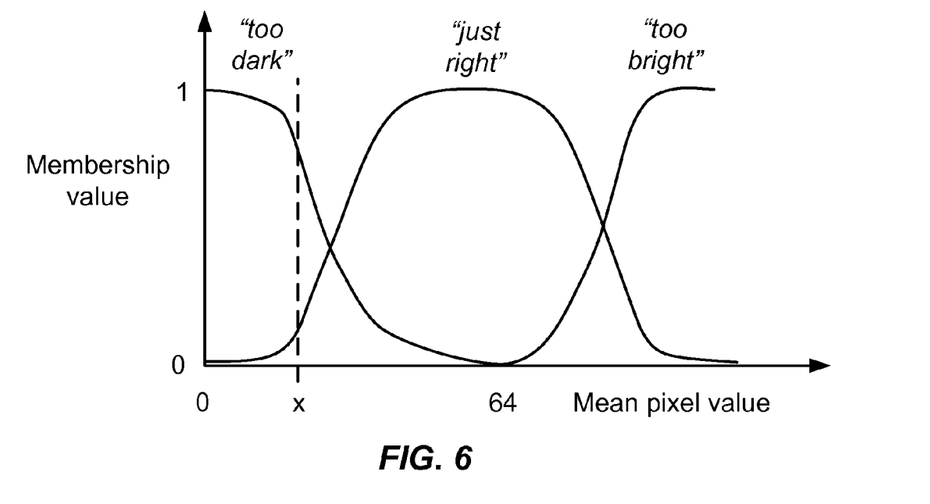
FIG. 6 is a diagram illustrating membership functions for fuzzifying mean echo levels according to an embodiment of the present invention.

Fuzzy logic provides a framework for dealing with imprecise terms such as too large, too bright and appropriate amount. The first step (see FIG. 3) is to fuzzify the input (mean pixel value) in accordance to a set of pre-defined membership functions. Referring to FIG. 6, suppose the universe of ROI pixel intensity levels consists of 3 classes each defined by a membership function of membership value versus mean pixel value. The membership functions are named, in order of mean pixel value range:
1. "too dark"
2. "just right"
3. "too bright"

The membership value always ranges from 0 to 1, and measures the degree to which a particular input belongs to that membership class. The objective of adaptive gain control is to adjust the gain so that the mean pixel value falls within the class "just right," which may be centered around pixel value 64, for example.

The fact that the membership functions are overlapping implies that a given input may simultaneously belong to two or more distinct (even contradictory) classes, which is the essence of "fuzziness." The precise shape of the membership function is usually not of critical importance, as long as it matches the subjective judgment of the meaning of each class. Referring to FIG. 6, for a mean pixel value x, the membership value MV(k) of membership function k are MV(1)=0.8, MV(2)=0.2, MV(3)=0. That is, x is too dark with 0.8 membership value and just right with 0.2 membership value. The sum of all possible membership values at a given mean pixel value should be unity.

The second step (see FIG. 3) in fuzzy logic control is to apply a set of pre-defined inference rules, which represent how an expert user would adjust the gain given the membership values of all 3 membership functions. As a simple yet reasonable example, the set of inference rules are:
  1. If ROI is too dark, make a positive gain change.
  2. If ROI is just right, make zero gain change.
  3. If ROI is too bright, make a negative gain change.

For a given mean pixel value x, applying the inference rules means determining membership values or weight factors w(k), k=1,2,3, for the 3 possible classes of fuzzy outputs (gain changes):
  1. NEG: negative.
  2. ZE: zero.
  3. POS: positive.

In the above example, because the mapping of input membership function to gain change class is 1:1, the MVs of the 3 input classes can transfer directly to gain change weight factors. That is, Weight factor for a POS gain change w(1)=0.8 (too dark)

Weight factor for a ZE gain change w(2)=0.2 (Just right)

In general, however, inference rules can follow a highly complex hierarchical structure with many N:1 mappings, where N>1. For example, they may involve an independent fuzzy attribute that describes the ROI composition (noise-dominant or echo-dominant) based on computing the percentage of pixels within the ROI that have exceeded a system noise threshold. The inference rules may include MAX, MIN or AVERAGE operations in order to realize such N:1 mappings.

Figure 7:
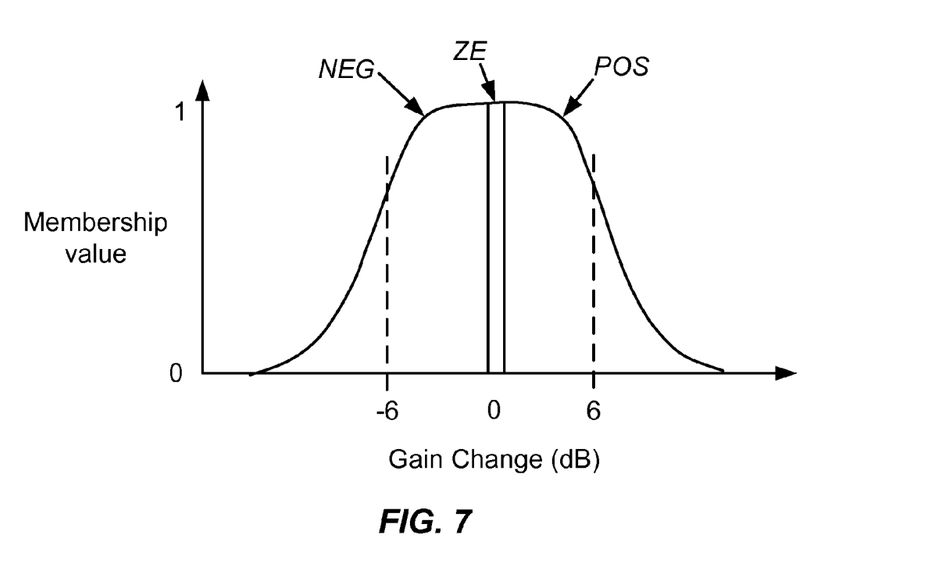
FIG. 7 is a diagram illustrating gain change membership functions according to an embodiment of the present invention.

The last step (see FIG. 3) is to defuzzify the fuzzy gain changes into a numerical value ΔG that feeds into the receiver gain controller (to be used for the next image frame). As shown in FIG. 7, the three classes of fuzzy gain changes form their own set of membership functions of membership value versus gain change. These functions are intended to model, at least subjectively, what an expert user would consider a negative, zero, and positive gain change. As described in Kosko's book, there are different methods for defuzzifying the prescribed outputs (gain changes). One method involves characterizing each gain change membership function by its centroid; i.e., a POS change is +6 dB, ZE is 0 dB, and a NEG change is −6 dB, and then setting the optimal gain change equal to the sum of centroids weighted by the corresponding w(k):

$$\text{Gain change (dB)} = +6 \cdot w(1) + 0 \cdot w(2) - 6 \cdot w(3)$$

Based on the non-zero weight factors in the present example, the optimal gain change is $$\text{Gain change (dB)} = 6 \cdot 0.8 + 0 \cdot 0.2 - 6 * 0 = +4.8$$

which can be applied to the next and future image data frames. Fuzzy control is often an iterative process. That is, the above fuzzy control process can be repeated as many times as necessary until the image is just right.

In the following, many more embodiments of the present invention that span one or more subsystems will be described for different functional categories. Simple examples of possible fuzzified inputs, inference rules, and fuzzified outputs will be provided. As for the above automatic gain control example, all of these embodiments are intended to be exemplary and non-limiting.

B-Image Optimization

This category pertains to fuzzy control of B-imaging parameters that are usually adjustable by the user. These include image processing parameters such as gain (front-end receiver analog and/or digital gain, and digital gain control within the image processor), dynamic range, frame averaging level and gray map, which control the SNR (signal-to-noise ratio), brightness, contrast, smoothness and persistence of the B-mode images.

Adaptive control can offer more degrees of freedom in, for example, optimizing persistence level and gain as a function of 2D location in the image, since the optimization is no longer limited by the finite resolution or incremental step size of manual control keys.

The fuzzy controller can receive input data at any point in the B-mode signal path, and prescribe changes to imaging parameters in either a feedback or feed-forward manner.

In another embodiment, both the transmit and receive subsystem setups including the transmit waveform (pulse length, shape and center frequency), receive center frequencies and filter bandwidths, focal zone depths, and apertures for different focal zones are adjusted automatically by the fuzzy logic controller. The inputs for this application include fuzzified image quality attributes based on the current B-image data. Examples of inference rules include:

"If SNR in far field is poor, switch to a lower center frequency;"

"If patient type is easy, switch to higher center frequency for better resolution;"

"If the central portion of the image is hazy, switch to tissue harmonic imaging."

In another embodiment, the basic user-controls for M-mode such as dynamic range and sweep speed can be automated via fuzzy logic.

Another embodiment involves monitoring the channel-to-channel coherence characteristics in the receiver subsystem, and then tailoring the transmit and/or receive focusing delay profile to the tissue properties of different regions in the body being scanned. An example of a fuzzy logic inference rule is "If the signal coherence between a pair of adjacent channels is poor, change the relative time delay for those two channels by a small amount."

Color Flow Image Optimization

As for B-mode, one embodiment of color flow image optimization via fuzzy logic is to automatically adjust both the transmit and receive subsystems including the transmit waveform (pulse length, shape and center frequency), pulse repetition frequency (PRF), flow sample count or packet size (number of transmit firings to form one color acoustic line), receive center frequencies and filter bandwidths, focal zone depths, and apertures for different focal zones, based on fuzzified measures of the current color flow image data. Examples of inference rules include:

"If overall SNR is very poor, use a higher flow sample count"

"If the mean velocities of a majority of color pixels are low, switch to a lower PRF."

In another embodiment, fuzzy logic is applied to adaptively optimize image processing parameters based on the current image data. The parameters that can be adjusted include those that affect image persistence, flash suppression (due to breathing and/or probe/patient motion), overall brightness and contrast. Examples of inference rules include:

"If the display amplitude range of a power Doppler image is low, switch to a lower dynamic range."

"If velocity changes from frame to frame are large, make a medium increase in persistence filtering."

In another embodiment, fuzzy logic is employed to automatically activate the optimal combination of algorithm blocks (e.g., wall filter, velocity estimation method, smoothing filter) depending on the fuzzified flow situation as measured from the current image data. An inference rule example is:

"If current image shows mostly lowflow and small vessels, switch to an IIR (infinite impulse response) wall filter and correlation-based velocity estimator."

In another embodiment, a coarse-resolution (in space and time) survey mode is used to first identify regions where flow exists. A fuzzy logic controller is then used to position a color flow "pan box" of appropriate size to capture and track the flow region with normal or high resolution scanning.

Spectral Doppler Image Optimization

One embodiment for spectral Doppler image optimization is to automatically adjust both the transmit and receive subsystems including the transmit waveform (pulse length and center frequency), pulse repetition frequency (PRF), filter bandwidths and transmit/receive apertures, based on fuzzified measures of current spectral waveform image data. An inference rule example is:

"If the spectral SNR is poor, switch to a lower transmit center frequency."

In another embodiment, fuzzy logic is used to automate any to all of the standard front-panel controls for spectral Doppler display optimization. These include but are not limited to master gain, PRF, baseline shift, spectrum invert, display dynamic range, gray or color maps, and sweep speed. Inference rule examples include:

"If the current spectral waveform is one-sided and slightly aliased, set baseline position lower"

"If the current spectral waveform is severely aliased, switch to a higher PRF."

"If the current spectral waveform intensity is only slightly above the noise floor, switch to a lower display dynamic range."

Another embodiment is to use a neural-network-trained fuzzy logic controller to automatically identify, for a given application type (e.g., carotid), the main vessel (e.g., carotid artery) location in the B-mode image, and determine its spatial orientation based upon which the best beam steer angle and Doppler angle can be computed. The system will further automatically position a tracking sample volume gate of appropriate size at or near the center of the lumen of a moving vessel.

In another embodiment, fuzzy logic is employed to automatically detect and trace out the envelope of the spectral waveform in real-time. It can further be used to automatically separate out representative cardiac cycles from those that are deemed poor quality or corrupted by patient/probe motion. A representative spectral trace can then be used to compute various standard diagnostic indices such as systolic to diastolic ratio. Like cardiac borders, the envelope of the spectral waveform is intrinsically fuzzy; hence fuzzy logic is expected to be well-suited for automatic waveform tracing.

Optimization of New or Emerging Imaging Modes

For new or emerging imaging modes such as functional imaging, contrast agent imaging, gray-scale flow ("B-flow") imaging, spatial and frequency compounded imaging, 3D imaging, sono-elasticity and parametric imaging, to name a few, fuzzy logic should also find applications similar to those described above. In fact, some existing techniques use fuzzy logic for image registration in 3D and spatial compounding applications.

Neural-fuzzy systems can conceivably be applied to a fusion mode wherein a composite image of two or more complementary image modalities (e.g., MRI, CT, x-ray) is formed. The fuzzy logic controller obtains estimates of the best features from each image modality (e.g., bones from x-ray, and soft tissue data from ultrasound), determines the best spatial registration of the different image data, and then generates a composite image accordingly.

Automated Image Analysis

There are known methods for automated detection of tumors, and abnormalities even in the presence of contrast agents. New potential applications include other types of tissue characterization (e.g., liver, prostate, artery/vein differentiation) and biopsy needle tracking.

Overall System Control & Optimization

This category includes without limitation acoustic power/thermal control, automatic shutdown of idling subsystems, optimization of battery power utilization, and system self-diagnosis or remote diagnosis.

It is well known that the acoustic output models that relate transmit voltages and duty cycle to acoustic output dosage and safety indices such as the mechanical index, thermal index and intensity spatial peak temporal average (ISPTA), are highly nonlinear. Conventional systems provide the user with a manual control for acoustic output, where 100% represents the predicted maximum allowable output without exceeding safety margins. In practice, from both a patient safety and battery-power conservation standpoint, it is highly desirable to minimize output levels whenever the returning ultrasound signal is stronger than needed—without relying on the user to manually adjust the acoustic output control. Thus, in one embodiment, fuzzy logic provides the way for automatic adjustments of transmit voltages and/or frame rates (duty cycles) in accordance with the principle of ALARA (as low as reasonably achievable). A specific inference rule example is:

If the signal-to-noise ratios in pre-defined regions of a color flow image are much stronger than needed, the transmit voltages for both the color flow and background B-mode image shall automatically be reduced.

It is conceivable that the manual acoustic output control (0-100%) can be completely replaced by an automatic ALARA control that ranges from conservative to aggressive. That is, the fuzzy ALARA setting directly controls the acoustic output reduction factor when the signal-to-noise ratios are high.

In another embodiment, the fuzzy controller is used to optimize system resources including DSP and memory usages, as a function of battery power level. Examples of inference rules include:

When the battery is running low, turn off certain system operations that produce incremental image quality benefits but consume a large amount of power.

In color flow mode, if the signal levels in the background B-mode image are strong, concentrate the acoustic power (voltage and/or number of firings per scan region) more in the color flow transmit firings.

It would be apparent to those skilled in the art that there are unlimited variations on how the fuzzy logic inference rules can be formulated or defined for various applications, and that the above are meant to serve as examples only. In practice, a complex hierarchy of inference rules may be needed for robust adaptive performance.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims along with their full scope of equivalents.

What is claimed is:

1. An ultrasound system comprising:
   a plurality of ultrasound image generating subsystems configured to generate an ultrasound image, the plurality of ultrasound image generating subsystems including a transmitter subsystem, a receiver subsystem, and an image processing subsystem; and
   a fuzzy logic controller communicatively coupled with at least one of the plurality of ultrasound imaging generating subsystems;
   wherein the fuzzy logic controller is configured to receive, from at least one of the plurality of ultrasound imaging generating subsystems, input data including at least one of pixel image data and data for generating pixel image data;
   wherein the fuzzy logic controller is configured to process the input data using a set of inference rules to produce fuzzy output;
   wherein the fuzzy logic controller is configured to convert the fuzzy output into numerical values or system states for controlling at least one of the transmit subsystem and the receiver subsystem that generate the pixel image data; and
   wherein the fuzzy logic controller is configured to adaptively adjust a plurality of system parameters, including transmit control, receiver gain control, receive focusing, and image processing parameters, for one or more imaging modes.

2. The ultrasound system of claim 1 wherein the set of inference rules used by the fuzzy logic controller are derived from at least one of (i) a predefined expert system that represents what an expert sonographer or a system engineer would do to control operations of at least one of the plurality of ultrasound image generating subsystems; and (ii) a neural network which can be trained to adapt functions of at least one of the ultrasound image generating subsystems.

3. The ultrasound system of claim 2 further comprising a neural network processor communicatively coupled with the fuzzy logical controller and at least one of the ultrasound image generating subsystems, the neural network processor being configured to adapt functions of at least one of the ultrasound image generating subsystems.

4. The ultrasound system of claim 3 wherein the neural network processor is configured to adapt functions of at least one of the ultrasound image generating subsystems based on at least one of different patient types, user preferences, and system operating conditions.

5. The ultrasound system of claim 1 wherein the fuzzy logic controller is configured to fiazzify the input data prior to processing input data using the set of inference rules, and wherein fuzzifying the input data comprises determining a degree of membership or membership value of the input data to a set of predefined input membership fUnctions or classes.

6. The ultrasound system of claim 1 wherein the system parameters include receiver gain control parameters for the receiver subsystem; and wherein the fuzzy logic controller is configured to adaptively adjust the receiver gain control parameters for the receiver subsystem to adjust the gain for different regions within the B-mode imaging, wherein adaptively adjusting the receiver gain control parameters for the receiver subsystem comprises:

analyzing a pixel intensity distribution in different predefined regions (ROI) of a detected image received by the receiver subsystem, based on a most recently processed series of one or more image frames that have been processed by the image processing subsystem;

for each ROI, computing a mean pixel intensity level and classifying the mean pixel intensity level based on a set of two or more predefined fuzzy membership functions for pixel intensity level;

for each ROI, computing a percentage of pixels that have exceeded a pre-determined system noise threshold and classifying the result based on a set of two or more predefined fuzzy membership functions for ROI composition;

applying a set of inference rules to evaluate gain change membership values of a set of predefined gain change membership functions;

defuzzifying the gain change membership values, by converting the gain change membership values into a numeric gain adjustment via a set of predefined equations that utilize the gain change membership values as weight factors, to obtain prescribed gain changes; and applying the prescribed gain changes to corresponding data segments for at least one or a current B-mode image frame and a future B-mode image frame.

7. The ultrasound system of claim 6 wherein the predefined fuzzy membership functions for mean pixel intensity level include "too dark," "just right," and "too bright"; wherein the predefined fuzzy membership functions for ROI composition include "noise-dominant" and "echo-dominant"; and wherein the predefined gain change membership functions include "positive," "zero," and "negative."

8. The ultrasound system of claim 6 wherein the image processing subsystem comprises a B-mode image processor including a detector, a log compression and filtering block, and a scan converter; and wherein the fuzzy logic controller is configured to read out the pixel image data from the B-mode image processor before or after the scan converter.

9. The ultrasound system of claim 1 wherein the system parameters further comprise at least one of:

transmit control parameters for the transmitter subsystem to specify at least one of transmit waveform, aperture function, delay profile, and pulsed repetition frequency for one or more imaging modes;

electronic array focusing parameters for the receiver subsystem to specify the receive aperture function as a function of time/depth and the time delay profiles for image reconstruction; and image processing parameters for the image processing subsystem to specify at least one of display dynamic range, gray or color maps, and spatial/temporal filtering.

10. The ultrasound system of claim 1 wherein the plurality of ultrasound image generating subsystems further include a transducer subsystem and an audio and video display subsystem.

11. An ultrasound system comprising:

a plurality of ultrasound image generating subsystems configured to generate an ultrasound image, the plurality of ultrasound image generating subsystems including a transmitter subsystem, a receiver subsystem, and an image processing subsystem; and a fuzzy logic controller communicatively coupled with at least one of the plurality of ultrasound imaging generating subsystems, wherein the fuzzy logic controller is configured to adaptively adjust parameters for at least B-mode imaging wherein the system parameters include receiver gain control parameters for the receiver subsystem;

the fuzzy logic controller including a fuzzy logic program stored in a computer readable storage medium;

wherein the fuzzy logic program includes:

code for receiving, from at least one of the plurality of ultrasound imaging generating subsystems, input data including at least one of pixel image data and data for generating pixel image data;

code for processing the input data using a set of inference rules to produce fuzzy output; and code for converting the fuzzy output into numerical values or system states for controlling at least one of the transmit subsystem and the receiver subsystem that generate the pixel image data; and code for adaptively adjusting the receiver gain control parameters for the receiver subsystem to adjust the gain for different regions within the B-mode imaging;

wherein the code for adaptively adjusting the receiver gain control parameters comprises:

code for analyzing a pixel intensity distribution in different pre-defined regions (ROI) of a detected image received by the receiver subsystem, based on a most recently processed series of one or more image frames that have been processed by the image processing subsystem;

code for computing, for each ROI, a mean pixel intensity level and classifying the mean pixel intensity level based on a set of two or more predefined fuzzy membership functions for pixel intensity level;

code for computing, for each ROI, a percentage of pixels that have exceeded a pre-determined system noise threshold and classifying the result based on a set of two or more predefined fuzzy membership functions for ROI composition;

code for applying a set of inference rules to evaluate gain change membership values of a set of predefined gain change membership functions;

code for defuzzifying the gain change membership values, by converting the gain change membership values into a numeric gain adjustment via a set of predefined equations that utilize the gain change membership values as weight factors, to obtain prescribed gain changes; and code for applying the prescribed gain changes to corresponding data segments for at least one or a current B-mode image frame and a future B-mode image frame.

12. The ultrasound system of claim 11 further comprising a neural network processor communicatively coupled with the fuzzy logical controller and at least one of the ultrasound image generating subsystems, the neural network processor including a neural network program stored in a computer-readable storage medium, the neural network program having code for adapting functions of at least one of the ultrasound image generating subsystems.

13. The ultrasound system of claim 11 wherein:

the fuzzy logic program includes code for fuzzifying the input data prior to processing input data using the set of inference rules, and fuzzifying the input data comprises determining a degree of membership or membership value of the input data to a set of predefined input membership functions or classes.

14. The ultrasound system of claim 11 wherein:
the image processing subsystem comprises a B-mode image processor including a detector, a log compression and filtering block, and a scan converter; and
the fuzzy logic program includes code for reading out the pixel image data from the B-mode image processor before or after the scan converter.

15. The ultrasound system of claim 11 wherein the system parameters further comprise at least one of:
transmit control parameters for the transmitter subsystem to specify at least one of transmit waveform, aperture function, delay profile, and pulsed repetition frequency for one or more imaging modes;
electronic array focusing parameters for the receiver subsystem to specify the receive aperture function as a function of time/depth and the time delay profiles for image reconstruction; and
image processing parameters for the image processing subsystem to specify at least one of display dynamic range, gray or color maps, and spatial/temporal filtering.

16. The ultrasound system of claim 11 wherein the plurality of ultrasound image generating subsystems further include a transducer subsystem and an audio and video display subsystem.

17. A method of processing data for generating an ultrasound image, the method comprising:
receiving, from at least one of a plurality of ultrasound imaging generating subsystems which include a transmitter subsystem, a receiver subsystem, and an image processing subsystem, input data including at least one of pixel image data and data for generating pixel image data;
adaptively adjusting system parameters for at least one imaging mode wherein the system parameters include receiver gain control parameters for the receiver subsystem wherein:
adaptively adjusting parameters comprises adaptively adjusting the receiver gain control parameters for the receiver subsystem to adjust the gain for different regions within B-mode imaging, wherein adaptively adjusting the receiver gain control parameter for the receiver subsystem comprises:
analyzing a pixel intensity distribution in different predefined regions (ROI) of a detected image received by the receiver subsystem, based on a most recently processed series of one or more image frames that have been processed by the image processing subsystem;
for each ROI, computing a mean pixel intensity level and classifying the mean pixel intensity level based on a set of two or more predefined fuzzy membership functions for pixel intensity level;
for each ROI, computing a percentage of pixels that have exceeded a pre-determined system noise threshold and classifying the result based on a set of two or more predefined fuzzy membership functions for ROI composition;
applying a set of inference rules to evaluate gain change membership values of a set of predefined gain change membership functions;
defuzzifying the gain change membership values, by converting the gain change membership values into a numeric gain adjustment via a set of predefined equations that utilize the gain change membership values as weight factors, to obtain prescribed gain changes; and
applying the prescribed gain changes to corresponding data segments for at least one of a current B-mode image frame and a future B-mode image frame.

18. The method of claim 17 further comprising deriving the set of inference rules from at least one of (i) a predefined expert system that represents what an expert sonographer or a system engineer would do to control operations of at least one of the plurality of ultrasound image generating subsystems; and (ii) a neural network which can be trained to adapt functions of at least one of the ultrasound image generating subsystems.

19. The method of claim 17 further comprising employing a neural network to adapt functions of at least one of the ultrasound image generating subsystems.

20. The method of claim 17 further comprising fuzzifying the input data prior to processing input data using the set of inference rules; wherein fuzzifying the input data comprises determining a degree of membership or membership value of the input data to a set of predefined input membership functions or classes.

21. The method of claim 17 wherein the parameters include transmit control, receiver gain control, receive focusing, and image processing parameters, and wherein the parameters are adaptively adjusted for one or more imaging modes.

22. The method of claim 17 wherein:
the predefined fuzzy membership functions for mean pixel intensity level include "too dark," "just right," and "too bright";
the predefined fuzzy membership functions for ROI composition include "noise-dominant"and "echo-dominant"; and
the predefined gain change membership functions include "positive," "zero," and "negative."

23. The method of claim 17 wherein the system parameters further comprise at least one of:
transmit control parameters for the transmitter subsystem to specify at least one of transmit waveform, aperture function, delay profile, and pulsed repetition frequency for one or more imaging modes;
electronic array focusing parameters for the receiver subsystem to specify the receive aperture function as a function of time/depth and the time delay profiles for image reconstruction; and
image processing parameters for the image processing subsystem to specify at least one of display dynamic range, gray or color maps, and spatial/temporal filtering.

\* \* \* \* \*

UNITED STATES PATENT AND TRADEMARK OFFICE
CERTIFICATE OF CORRECTION

| | | |
|---|---|---|
| PATENT NO. | : 7,627,386 B2 | Page 1 of 1 |
| APPLICATION NO. | : 10/961709 | |
| DATED | : December 1, 2009 | |
| INVENTOR(S) | : Mo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1291 days.

Signed and Sealed this

Second Day of November, 2010

David J. Kappos
*Director of the United States Patent and Trademark Office*